United States Patent [19]

Crikelair

[11] 4,276,281

[45] Jun. 30, 1981

[54] BURN TREATMENT

[76] Inventor: George F. Crikelair, 2500 SE 21st St., Fort Lauderdale, Fla. 33316

[21] Appl. No.: 183,979

[22] Filed: Sep. 4, 1980

[51] Int. Cl.$^3$ ............................................... A61K 37/48
[52] U.S. Cl. ...................................................... 424/84
[58] Field of Search .............................. 424/94, 78, 81

[56] References Cited

U.S. PATENT DOCUMENTS 3,864,477  2/1975  Thuillier et al. ........................ 424/94
4,122,158  10/1978  Schmitt .................................. 424/94

*Primary Examiner*—Sam Rosen
*Attorney, Agent, or Firm*—Oltman and Flynn

[57] ABSTRACT

Eschar is removed from mammalian skin burns by application of elastase to promote healing of the burned area by hastening the removal of the burn eschar. The elastase solution preferably comprises purified elastase in tris hydroxymethyl aminoethane buffer at about pH 8.8. The elastase ointment comprises purified elastase in acrylic acid polymer at pH of about 8.5 to 8.8.

2 Claims, No Drawings

BURN TREATMENT

SUMMARY OF THE INVENTION

This invention relates to the debriding of burns by the use of elastase.

In treating burns the use of an effective enzymatic debridement agent is particularly helpful since burned skin separates slowly without medications and even slower if such as topical antibiotics are applied as is so often these days.

Elastase is derived from the pancreas of mammals, particularly hogs. It is a serine protease with a molecular weight of 25,900 and consists of 240 amino acid residues, the sequence of which has been determined [Shotten, D. M. and Hartley, B. S.; Biochem J. 131, 643 (1973)]. Chromatographically purified elastase is available commercially from Worthington Biochemical Corporation, Freehold, N.J., and other sources.

Elastase is known to have proteolytic activity, as stated in U.S. Pat. No. 3,367,836 to Thuillier.

Other products and proteolytic enzymes are known to be used as burn debriders and for removal of necrotic tissues in ulcers and the like, as disclosed in U.S. Pat. No. 3,019,171 to Block et al, U.S. Pat. No. 3,208,908 to Maxwell et al, and U.S. Pat. No. 4,122,158 to Schmitt. None of these meet the rigid criterion established as totally satisfactory debriders of denatured collagen such as is caused by the burning of skin.

The present invention is based on the discovery that elastase is particularly effective as a debridement agent for removing eschar and other macromolecular debris from mammalian skin burns, thus promoting faster healing of the burned area by preparing it more rapidly for grafting.

DETAILED DESCRIPTION

In determining the efficacy of elastase as a debriding agent, adult Sprague-Dawley rats were anesthesized with ether, shaved and given a full thickness contact burn over an area of approximately 2 cm. by 3 cm. in the middle of the back, immediately caudal to the scapulas, using a steel strip heated in a Bunsen flame to inflict the burn. Biopsies sectioned for microscopic examination confirmed that a full thickness burn was produced over the entire area contacted by the heated strip.

Immediately after the burn was made a small plastic cup was adhesively secured in an inverted position around the burn, using "Eastman 910" cyanoacrylate adhesive, followed by the application of rapid setting epoxy cement around the initial seal to reinforce it. The inverted cup was filled with 15 ml of elastase solution, using a syringe and needle. The elastase solution contained purified elastase prepared in a Tris (hydroxymethyl)-aminomethane buffer at pH 8.8, as described by Gomori in Proc. Soc. Exp. Biol. Med. 62, 33 (1946). At this pH the elastase is maximally active.

I have determined that for optimum debridement the elastase concentration in the solution should have 2500 units of elastase activity per liter of solution. A unit of elastase activity is defined as the quantity of elastase required to solubilize one milligram of elastin in 20 minutes at 37° C., pH 8.8. Assays of elastase solutions in the above-identified Tris buffer were performed using the spectrophotometric technique described by Sacher et al in Proc. Soc. Exp. Biol. Med. 90, 323 (1955). Solution concentrations greater than 2500 u/l do not improve the debriding activity, and lower concentrations reduce it.

After exposure for 48 hours to the elastase solution in an isolation cage with food and water ad libitum, the rats were sacrificed and the cups were removed. Where the enzyme solution had optimum concentration (2500 u/l) it was found that the burn eschar had been substantially completely digested, and what remained could be wiped away easily. This left a wound base suitable for grafting.

A saturated elastase solution (6000 u/l) produced substantially the same eschar-digesting effect as the 2500 u/l solution in Tris buffer, pH 8.8.

Comparable results were obtained in treating a burn after a time delay of 48 hours from when the burn was inflicted on the rat. Much of the eschar had been digested by the solution and what remained could be brushed off easily, leaving a healthy looking base. These results were obtained with both the saturated elastase solution (6000 u/l) and the buffered 2500 u/l solution. Elastase has been used by me as a solution and in liquid form but it may also prove equally efficacious if put into an ointment or cream base which would serve as a carrier of the enzyme.

While the exact reasons for the very effective debriding action of elastase are not fully understood, it is believed that the following factors are significant:

(1) Elastin fibers are known to be more heat resistant than collagen fibers and may prolong the attachment of eschar to the burn wound [Vistnes, L. and Hogg, G.: The Burn Eschar. A Histopathological Study. Plastic and Reconstruction Surgery 48, 56–60 (1971)].

(2) Under normal circumstances, elastase degrades elastin rather specifically.

(3) Burn eschar is composed largely of denatured collagen and elastase digests heat-denatured collagen without attacking normal collagen [Banga, I.: Structure and Function of Elastin and Collagen. Budapest, Hungary, Akademiar Kiado, p. 46 (1966)].

There is evidence which indicates that the elastase is drawn out of the treatment solution by the eschar within one hour. Nonetheless, a satisfactory debridement did not take place in this time but instead required an exposure of about 48 hours to the solution. This indicates that the enzyme did not produce its full effect in the first hour despite the observed effect that no measurable elastase activity remained in the solution after the first hour.

Experiments to evaluate the acute toxicity of elastase indicate that it is substantially non-toxic to rats when injected intraperitoneally and subcutaneously, even where saturated elastase solution (6000 u/l) of as much as ten percent body weight (600 u/kg) was used. The same non-toxicity was observed in rats which received injections of elastase (3000 u/l) in Tris buffer, pH 8.8, in doses of five percent of body weight, corresponding to 150 u/kg.

Experiments also showed that elastase has no deleterious effect on normal or injured skin. This is true as to both elastase (2500 u/l) in Tris buffer at pH 8.8 and saturated elastase solution (6000 u/l). The injured skin was prepared by several different techniques:

(1) by surgical removal of a piece of full thickness skin;

(2) by intradermal injection of saline solution, followed by scalpel excision of surface skin;

(3) as a split thickness skin graft doner site; and
(4) by full thickness contact burns under anesthesia.

In the case of the granulating wound, (1) above, the elastase solutions were applied to a fresh wound and after exposure of the wound for 48 hours before the elastase was applied. Also, the full thickness contact burns were treated both as fresh wounds and after a 48 hour delay.

Elastase can be prepared as an ointment using Carbopol 934 P resin as the base. Carbopol 934 P is an acrylic acid polymer which is produced by the B. F. Goodrich Chemical Company, Cleveland, Ohio. When mixed in distilled water, it gives an acidic suspension which polymerizes instantly and becomes a high viscosity gel when neutralized with an appropriate base. The viscosity and pH of the final preparation can be adjusted by changing the concentration of the Carbopol suspension and the amount of base added, respectively.

Considerable toxicological data exists for Carbopol 934 P. In human testing it was found to be non-irritating and non-allergenic when applied to normal skin.

For use with elastase, the final ointment should have an enzyme concentration of 5000 to 7000 u/l, pH 8.5 to 8.8. It is prepared by mixing one part 1.8% Carbopol 934 P with approximately two parts elastase solution and adding one molar Tris to a concentration equaling 10% of the final volume.

For example, to make 75 ml 5000 u/l ointment mix at the same time:

25 ml 1.8% Carbopol 934 P in distilled water
42.5 ml 8800 u/l elastase in Tris buffer (Gomori), pH 8.8
7.5 ml one molar Tris This will make a fairly thin ointment, with a Carbopol resin concentration of 0.6%. It can be thickened by increasing the Carbopol concentration to 0.8%, but this may reduce the effective activity of the enzyme.

Because of the high concentration of elastase required to make the initial solution, it is necessary to use the chromatographically prepared lyophillized form of elastase rather than the 2 x crystallized suspension, which is much less soluble in water.

The ointment is placed on the burn and covered in some fashion so it cannot be rubbed off. The ointment should be changed two or three times daily, and the wound should be wiped with gauze to remove digested material when the ointment is replaced.

I claim:
1. A method of treating burned mammalian tissue which comprises contacting the burned tissue with elastase in a concentration effective to substantially digest the burn eschar.
2. A method of debriding an animal burn without substantial injury to adjacent living tissue which comprises contacting the burned tissue with elastase in a concentration effective to substantially digest the burn eschar.

* * * * *